(12) United States Patent
Cohen et al.

(10) Patent No.: US 10,736,876 B2
(45) Date of Patent: Aug. 11, 2020

(54) IDALOPIRDINE-BASED COMBINATORIAL THERAPIES OF ALZHEIMER'S DISEASE

(71) Applicant: PHARNEXT, Issy les Moulineaux (FR)

(72) Inventors: Daniel Cohen, Saint Cloud (FR); Serguei Nabirochkin, Chatenay Malabry (FR); Rodolphe Hajj, Saint Germain en Laye (FR); Anthony Brureau, Chilly-Mazarin (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

(21) Appl. No.: 16/607,418

(22) PCT Filed: Apr. 23, 2018

(86) PCT No.: PCT/EP2018/060284
§ 371 (c)(1),
(2) Date: Oct. 23, 2019

(87) PCT Pub. No.: WO2018/197383
PCT Pub. Date: Nov. 1, 2018

(65) Prior Publication Data
US 2020/0129479 A1    Apr. 30, 2020

(30) Foreign Application Priority Data
Apr. 24, 2017 (EP) .................................. 17305462

(51) Int. Cl.
*A61K 31/404* (2006.01)
*A61P 25/28* (2006.01)
*A61K 31/195* (2006.01)

(52) U.S. Cl.
CPC .......... *A61K 31/404* (2013.01); *A61K 31/195* (2013.01); *A61P 25/28* (2018.01)

(58) Field of Classification Search
CPC ...... A61K 31/195; A61K 31/404; A61P 25/28
See application file for complete search history.

(56) References Cited

U.S. PATENT DOCUMENTS

| | | |
|---|---|---|
| 8,552,041 B2 | 10/2013 | Cohen et al. |
| 8,741,886 B2 | 6/2014 | Cohen et al. |
| 8,809,302 B2 | 8/2014 | Cohen et al. |
| 8,865,769 B2 | 10/2014 | Cohen et al. |
| 9,144,558 B2 | 9/2015 | Cohen et al. |
| 9,241,933 B2 | 1/2016 | Cohen et al. |
| 9,248,111 B2 | 2/2016 | Cohen et al. |
| 9,387,206 B2 | 7/2016 | Cohen et al. |
| 9,636,316 B2 | 5/2017 | Cohen et al. |
| 9,820,978 B2 | 11/2017 | Cohen et al. |
| 9,867,837 B2 | 1/2018 | Cohen et al. |
| 9,931,326 B2 | 4/2018 | Cohen et al. |
| 10,004,744 B2 | 6/2018 | Cohen et al. |
| 10,010,515 B2 | 7/2018 | Cohen et al. |
| 10,045,971 B2 | 8/2018 | Cohen et al. |
| 10,342,768 B2 | 7/2019 | Cohen et al. |
| 10,342,784 B2 | 7/2019 | Cohen et al. |
| 10,350,195 B2 | 7/2019 | Cohen et al. |
| 10,434,109 B2 | 10/2019 | Cohen et al. |
| 2011/0269764 A1 | 11/2011 | Cohen et al. |
| 2012/0058992 A1 | 3/2012 | Cohen et al. |
| 2012/0071483 A1 | 3/2012 | Cohen et al. |
| 2012/0270836 A1 | 10/2012 | Cohen et al. |
| 2013/0085122 A1 | 4/2013 | Cohen et al. |
| 2013/0090307 A1 | 4/2013 | Cohen et al. |
| 2014/0038927 A1 | 2/2014 | Cohen et al. |
| 2014/0080873 A1 | 3/2014 | Cohen et al. |
| 2014/0357648 A1 | 12/2014 | Cohen et al. |
| 2014/0371229 A1 | 12/2014 | Cohen et al. |
| 2014/0371277 A1 | 12/2014 | Cohen et al. |
| 2014/0378440 A1 | 12/2014 | Cohen et al. |
| 2015/0246044 A1 | 9/2015 | Cohen et al. |
| 2016/0000736 A1 | 1/2016 | Cohen et al. |
| 2016/0136136 A1 | 5/2016 | Cohen et al. |
| 2016/0136143 A1 | 5/2016 | Cohen et al. |
| 2016/0193163 A1 | 7/2016 | Cohen et al. |
| 2016/0206603 A1 | 7/2016 | Cohen et al. |
| 2017/0231958 A1 | 8/2017 | Cohen et al. |
| 2017/0273919 A1 | 9/2017 | Cohen et al. |
| 2018/0125867 A1 | 5/2018 | Cohen et al. |
| 2018/0263989 A1 | 9/2018 | Cohen et al. |
| 2018/0338988 A1 | 11/2018 | Cohen et al. |
| 2018/0344711 A1 | 12/2018 | Cohen et al. |
| 2019/0175568 A1 | 6/2019 | Cohen et al. |
| 2019/0298698 A1 | 10/2019 | Cohen et al. |

FOREIGN PATENT DOCUMENTS

| WO | WO 2009/133128 | 11/2009 |
|---|---|---|
| WO | WO 2009/133141 | 11/2009 |
| WO | WO 2009/133142 | 11/2009 |

(Continued)

OTHER PUBLICATIONS

Chumakov, I. et al. "Combining two repurposed drugs as a promising approach for Alzheimer's disease therapy" *Scientific Reports*, Jan. 8, 2015, pp. 1-12, vol. 5.
Galimberti, D. et al. "Idalopirdine as a treatment for Alzheimer's disease" *Expert Opinion on Investigational Drugs*, 2015, pp. 981-987, vol. 24, No. 7.
Taylor, N. P. "Lundbeck calls time on Alzheimer's drug after more failures" Feb. 8, 2017, pp. 1-3, XP-002774294, Retrieved from the Internet: URL:http://www.fiercebiotech.com/biotech/lundbeck-calls-time-alzheimer-s-drug-after-more-Failure, retrieved on Feb. 8, 2017.
Wicke, K. et al. "Investigational drugs targeting 5-HT6 receptors for the treatment of Alzheimer's disease" *Expert Opinion on Investigational Drugs*, 2015, pp. 1515-1528, vol. 24, No. 12.
Written Opinion in International Application No. PCT/EP2018/060284, May 25, 2018, pp. 1-7.

(Continued)

*Primary Examiner* — Joseph R Kosack
(74) *Attorney, Agent, or Firm* — Saliwanchik, Lloyd & Eisenschenk (57) ABSTRACT

The present invention relates to combinatorial therapies and methods for the treatment of Alzheimer's disease or an Alzheimer's disease related disorder based on idalopirdine, baclofen and acamprosate, wherein idalopirdine is provided as suboptimal doses.

11 Claims, 3 Drawing Sheets

(56) References Cited

FOREIGN PATENT DOCUMENTS

WO  WO 2011/054759  5/2011
WO  WO 2012/117076  9/2012

OTHER PUBLICATIONS

Wilkinson D, et al., "Safety and efficacy of idalopirdine, a 5-HT6 receptor antagonist, in patients with moderate Alzheimer's disease (LADDER): a randomised, double-blind, placebo-controlled phase 2 trial" *The Lancet Neurology*, Nov. 1, 2014, pp. 1092-1099, vol. 13, Issue 11.
Atri, A. et al., "Effect of Idalopirdine as Adjunct to Cholinesterase Inhibitors on Change in Cognition in Patients With Alzheimer Disease" *JAMA*, Jan. 9, 2018, pp. 130-142, vol. 319, No. 2.

IDALOPIRDINE-BASED COMBINATORIAL THERAPIES OF ALZHEIMER'S DISEASE

CROSS-REFERENCE TO RELATED APPLICATION

This application is the U.S. national stage application of International Patent Application No. PCT/EP2018/060284, filed Apr. 23, 2018.

FIELD OF THE INVENTION

The present invention relates to new combinations and methods for the treatment of Alzheimer's disease and related disorders. More specifically, the present invention relates to novel combinatorial therapies of Alzheimer's disease and related disorders based on combinations of idalopirdine, baclo fen and acamprosate.

BACKGROUND OF THE INVENTION

Alzheimer's disease (AD) is the prototypic cortical dementia characterized by memory deficit together with dysphasia (language disorder in which there is an impairment of speech and of comprehension of speech), dyspraxia (disability to coordinate and perform certain purposeful movements and gestures in the absence of motor or sensory impairments) and agnosia (inability to recognize objects, persons, sounds, shapes, or smells) attributable to involvement of the cortical association areas. Special symptoms such as spastic paraparesis (weakness affecting the lower extremities) can also be involved [1-4].

Incidence of AD increases dramatically with the age. AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis [5]. United Nations population projections estimate that the number of people older than 80 years will approach 370 million by the year 2050. Currently, it is estimated that 50% of people older than age 85 years are afflicted with AD. Therefore, more than 100 million people worldwide will suffer from dementia in 50 years. The vast number of people requiring constant care and other services will severely affect medical, monetary and human resources [6].

Memory impairment is the early feature of the disease and involves episodic memory (memory for day-to-day events). Semantic memory (memory for verbal and visual meanings) is involved later in the disease. By contrast, working memory (short-term memory involving structures and processes used for temporarily storing and manipulating information) and procedural memory (unconscious memory that is long-term memory of skills and procedure) are preserved until late. As the disease progresses, the additional features of language impairment, visual perceptual and spatial deficits, agnosias and apraxias emerge.

The classic picture of AD is sufficiently characteristic to allow identification in approximately 80% of cases [7]. Nevertheless, clinical heterogeneity does occur which is important for clinical management but also provides further implication of specific medication treatments for functionally different forms [8].

The pathological hallmarks of AD include deposition of extracellular amyloid plaques containing beta-amyloid peptides (Abeta), intracellular neurofibrillary tangles mainly composed of Tau protein and progressive neuronal and synaptic dysfunction and loss [9-11]. The etiology of Alzheimer's disease (AD) remains elusive, and for the last decades, several main hypotheses on the cause of AD have been proposed: the "cholinergic hypothesis" attributing a particular role for decreased acetylcholinergic signaling in development of AD, the "amyloid cascade hypothesis", which states that the neurodegenerative process is a series of events provoked by the abnormal processing of the Amyloid Precursor Protein (APP) [12], the revised "Tau hypothesis" [13], which proposes that cytoskeletal changes are the triggering pathological events, and recently, neuroimmunomodulation hypothesis prioritizing changes in immune signaling in AD etiology and progression [19]. The most widely accepted theory explaining AD progression remains the amyloid cascade hypothesis [14-16] and AD researchers have mainly focused on determining the mechanisms underlying the toxicity associated with amyloidogenic Abeta peptides. Importantly, changes in microvascular permeability and vessels remodeling, manifested as aberrant angiogenesis and blood brain barrier breakdown in course of AD, have been identified as key events implicated to the APP toxicity [17].

Synaptic density change is a pathological lesion that correlates better with cognitive impairment than the depositions of APP and Tau aggregates. Studies have revealed that the amyloid pathology appears to progress in a neurotransmitter-specific manner where the cholinergic terminals appear most vulnerable, followed by the glutamatergic terminals and finally by the GABAergic terminals [11]. Glutamate is the most abundant excitatory neurotransmitter in the mammalian nervous system, and its functional effects are finely contra-balanced by GABAergic inhibitory neuronal receptors. Under pathological conditions, abnormal accumulation of glutamate in the synaptic cleft leads to glutamate receptors overactivation [18], that results in cognitive dysfunction and finally in neuronal cell death. This process, named excitotoxicity, is commonly observed in neuronal tissues during acute and chronic neurological disorders and is recognized now as one of the major pathological triggers in AD. Moreover, dysfunction in inhibitory GABA-mediated neuronal circuits observed in AD could increase negative consequences of dysregulated glutamate signaling in neuronal cells.

Up to now, two kinds of medications, accounting for only five drugs approved in most countries, are used for improving or slowing down symptoms of AD which lay on some acetylcholinesterase modulators and a blocker of NMDA glutamate Receptors (NMDAR) [20-22].

Acetylcholinesterase inhibitors such as donepezil, rivastigmine, tacrine and galantamine are currently available in the market and are efficient in symptomatic relief with beneficial effects on cognitive, functional and behavioral symptoms [23].

NMDAR antagonists that target various sites of this receptor have been tested to counteract excitotoxicity. Uncompetitive NMDAR antagonists target the ion channel pore thus reducing the calcium entry into postsynaptic neurons. Only one of them, namely memantine, reached the approval status in moderate to severe AD. This molecule is however of limited benefit in most AD patients, because it has only modest symptomatic effects and further has shown no significant effects in mild Alzheimer's disease [24,25]. Furthermore many other NMDAR antagonists have failed in advanced clinical trials for several neurodegenerative disorders [21,26,27]. Another approach in limiting excitotoxicity consists in inhibiting the presynaptic release of glutamate.

WO2009/133128, WO2009/133141, WO2009/133142, WO2011/054759, and WO2012/117076 disclose drug combinations suitable for use in the treatment of AD. WO2012/117076 particularly discloses the therapeutic efficacy of baclofen-acamprosate combination in AD, including for the protection of glutamate toxicity and/or Abeta toxicity. U.S. Pat. No. 9,144,558, which derives from WO2012/117076, also discloses the use of a combination of baclofen and acamprosate for the treatment of AD. U.S. Pat. No. 9,144,558 also describes a list of compounds that could be further combined with baclofen and acamprosate. U.S. Pat. No. 9,144,558, however, does not teach that a combination of idalopirdine, baclofen and acamprosate may display an effect at suboptimal doses of idalopirdine, let alone that it would result in a synergistic effect.

Idalopirdine is a selective 5-HT6 receptor antagonist that has shown some efficacy in treating AD and has been under clinical trial as an add-on therapy for donepezil [55, NCT02079246].

Despite active research in this area, there is still a need for alternative or improved efficient therapies for Alzheimer's disease and Alzheimer's related disorders.

SUMMARY OF INVENTION

The present invention provides new therapeutic methods and compositions suitable for treating Alzheimer's disease and Alzheimer's related disorders, particularly associated with Abeta oligomer toxicity and cognitive decline. More particularly, the invention relates to compositions comprising idalopirdine, baclofen and acamprosate, as well as to the use thereof for treating Alzheimer's disease or an Alzheimer's related disorder.

The invention stems, inter alia, from the unexpected discovery by the inventors that the combination of idalopirdine, baclofen and acamprosate, wherein idalopirdine is provided at suboptimal doses, particularly strongly protects from cognitive impairment, a symptom present in Alzheimer's disease and Alzheimer's related disorders.

Thus, combinations of idalopirdine, baclofen and acamprosate, wherein idalopirdine is provided at suboptimal doses, constitute an efficient and safer treatment for patients suffering from, predisposed to, or suspected to suffer from Alzheimer's disease or an Alzheimer's related disorder.

An object of this invention therefore relates to compositions or combinations comprising idalopirdine, baclofen and acamprosate, wherein idalopirdine is provided at suboptimal doses. Preferably, the invention relates to compositions comprising idalopirdine, baclofen and acamprosate, wherein idalopirdine is provided at a suboptimal dose, and wherein baclofen and/or acamprosate are provided at suboptimal doses. More preferably, the invention relates to compositions comprising idalopirdine, baclofen and acamprosate, wherein idalopirdine is provided at a suboptimal dose, and wherein the combination of baclofen and acamprosate is provided at a suboptimal dose.

The invention also relates to a composition or combination comprising a synergistic amount of idalopirdine, baclofen and acamprosate, or salts, prodrugs or derivatives thereof.

The invention also relates to a composition or combination comprising (i) between 0.05 mg and 100 mg idalopirdine or a salt, prodrug or derivative thereof; (ii) between 0.005 mg and 50 mg baclofen or a salt, prodrug or derivative thereof; and (iii) between 0.0005 mg and 100 mg acamprosate or a salt, prodrug or derivative thereof.

A further object of the invention also resides in a composition or combination comprising, consisting essentially of or consisting of:
- idalopirdine or a pharmaceutically acceptable salt, hydrate, derivative, isomer, racemate, or prodrug thereof, of any chemical purity,
- baclofen or a pharmaceutically acceptable salt, hydrate, derivative, isomer, racemate, or prodrug thereof, of any chemical purity, and
- acamprosate, or a pharmaceutically acceptable salt, hydrate, derivative, isomer, racemate, or prodrug thereof, of any chemical purity.

As will be further disclosed in the present application, the compounds in the combinations or compositions of the invention may be formulated separately or together. Also, they may be administered simultaneously, separately, sequentially or subsequently to a subject. They can also be administered repeatedly to a subject.

The compositions of the invention typically further comprise one or several pharmaceutically acceptable excipients or carriers. Also, the compounds as used in the present invention may be in the form of a salt, hydrate, ester, ether, acid, amide, racemate, isomer, enantiomerically pure composition or conjugates. They may also be in the form of sustained-release formulations. Prodrugs or derivatives of the compounds may be used as well.

In a preferred embodiment, a compound is used as such or in the form of a salt, hydrate, ester, ether or sustained release form thereof.

In another preferred embodiment, a prodrug or derivative is used.

A further object of this invention is a method of preparing a pharmaceutical composition, the method comprising mixing idalopirdine, baclofen and acamprosate in a pharmaceutically acceptable excipient or carrier.

A further object of the invention relates to compositions or combinations as defined above for use in the treatment of Alzheimer's disease (AD) or an AD related disorder.

Another object of this invention relates to a method for treating AD or an AD related disorder in a mammalian subject in need thereof, preferably a human subject in need thereof, the method comprising administering to said subject an effective amount of a composition or combination as defined above.

A preferred object of this invention relates to a method for treating AD or an AD related disorder in a mammalian subject in need thereof, preferably a human subject in need thereof, the method comprising simultaneously, separately, sequentially or subsequently administering to said subject an effective amount of idalopirdine, baclofen and acamprosate, wherein idalopirdine is administered at a suboptimal dose. Preferably idalopirdine is administered at a suboptimal dose, and baclofen and/or acamprosate are administered at suboptimal doses. Even more preferably idalopirdine is administered at a suboptimal dose, and the combination of baclofen and acamprosate is administered at a suboptimal dose.

The invention may be used for treating Alzheimer's disease or an Alzheimer's disease related disorder in any mammalian subject, preferably in any human subject, at any stage of the disease. As it will be disclosed in the examples, the compositions of the invention are able to ameliorate the pathological condition of said subjects.

BRIEF DESCRIPTION OF THE FIGURES

In FIG. 1A, groups were as follows: (1) Sc.$A\beta_{25-35}$; (2) $A\beta_{25-35}$; (3) $A\beta_{25-35}$/Acamprosate (0.032 mg/kg); (4) $A\beta_{25-35}$/baclofen (0.480 mg/kg); (5) $A\beta_{25-35}$/idalopirdine (4.5 mg/kg) and (6) baclofen, acamprosate and idalopirdine (respectively 0.480 mg/kg, 0.032 mg/kg and 4.5 mg/kg). In FIG. 1B, groups were as follows: (1) Sc.$A\beta_{25-35}$; (2) $A\beta_{25-35}$; (3) $A\beta_{25-35}$/baclofen and acamprosate (respectively 0.480 mg/kg and 0.032 mg/kg); (4) $A\beta_{25-35}$/acamprosate and idalopirdine (respectively 0.032 mg/kg and 4.5 mg/kg); (5) $A\beta_{25-35}$/baclofen and idalopirdine (respectively 0.480 mg/kg and 4.5 mg/kg); and (6) $A\beta_{25-35}$/baclofen, acamprosate and idalopirdine (respectively 0.480 mg/kg, 0.032 mg/kg and 4.5 mg/kg). Data are represented as mean and SEM. Anova followed by a Dunnett's test (vs $A\beta_{25-35}$) (* p-value <0.5;  p-value <0.01; * p-value <0.001; j**** p-value <0,0001). T*he effect was significantly synergistic* (S) *for the combination of three compounds against any composition of two compounds or drugs alone.*

In FIGS. 2A and 2C, groups were as follows: (1) Sc.$A\beta_{25-35}$; (2) $A\beta_{25-35}$; (3) $A\beta_{25-35}$/Acamprosate (0.032 mg/kg); (4) $A\beta_{25-35}$/baclofen (0.480 mg/kg); (5) $A\beta_{25-35}$/idalopirdine (4.5 mg/kg) and (6) $A\beta_{25-35}$/baclofen, acamprosate and idalopirdine (respectively 0.480 mg/kg, 0.032 mg/kg and 4.5 mg/kg). In FIGS. 2B and 2D, groups were as follows: (1) Sc.$A\beta_{25-35}$; (2) $A\beta_{25-35}$; (3) $A\beta_{25-35}$/baclofen and acamprosate (respectively 0.480 mg/kg and 0.032 mg/kg); (5) $A\beta_{25-35}$/acamprosate and idalopirdine (respectively 0.032 mg/kg and 4.5 mg/kg); (6) baclofen and idalopirdine (respectively 0.480 mg/kg and 4.5 mg/kg); and (7) baclofen, acamprosate and idalopirdine (respectively 0.480 mg/kg, 0.032 mg/kg and 4.5 mg/kg). Data are represented as mean and SEM. Kruskal-Wallis followed by a Dunn's test (vs $A\beta_{25-35}$) (* p-value <0.5;  p-value <0.01; * p-value <0.001; **** p-value <0,0001). The effect was significantly synergistic (S) for the combination of three compounds against any composition of two compounds or drugs alone.

DETAILED DESCRIPTION OF THE INVENTION

The present invention provides new methods and compositions for treating Alzheimer's disease (AD) or an AD related disorder. The invention discloses novel combinations of active compounds which allow an effective correction of such diseases and may be used in any mammalian subject.

More particularly, the invention provides novel compositions comprising idalopirdine, baclofen and acamprosate, wherein idalopirdine is provided at suboptimal doses, preferably idalopirdine is provided at suboptimal doses and baclofen and/or acamprosate are provided at suboptimal doses, even more preferably idalopirdine is provided at suboptimal doses and baclofen and acamprosate are provided at doses where the combination of baclofen and acamprosate is suboptimal.

As illustrated in the examples, the presence of idalopirdine, baclofen and acamprosate, wherein idalopirdine is provided at a suboptimal dose, surprisingly causes a synergistic neuroprotective effect against Abeta oligomer toxicity and cognitive impairment. The invention is therefore suited for treating AD or AD related disorders.

Definitions

The term "AD related disorder" designates disorders associated with Abeta oligomer toxicity and/or cognitive decline, and includes notably senile dementia of AD type (SDAT), frontotemporal dementia (FTD), vascular dementia, mild cognitive impairment (MCI) and age-associated memory impairment (AAMI).

As used herein, the term "treatment" includes the therapy, prevention, prophylaxis, retardation or reduction of symptoms provoked by or of the causes of the above diseases or disorders. The term treatment includes in particular the control of disease progression and associated symptoms. The term treatment particularly includes a protection against the toxicity caused by beta amyloid (also referred to as Abeta or $A\beta$), or a reduction or retardation of said toxicity, oxidative stress, neuroinflammation, and/or neuronal cell death. The term treatment particularly designates an improvement or attenuation of cognitive symptoms or a protection against Abeta toxicity.

One remarkable advantage of the invention is that each compound may be used at low doses, or suboptimal doses, in a combination therapy, while producing, in combination, a substantial clinical benefit to the patient. Accordingly, a particular advantage of the invention lies in the ability to use suboptimal doses of each compound. As used herein, the term "suboptimal dose(s)" of a compound or combination of compounds refers to dose(s) where the compound or combination has low or essentially no effect. For instance, a suboptimal dose of idalopirdine is a dose at which said compound, alone, has low or essentially no effect. A suboptimal dose of baclofen is a dose at which said compound, alone, has low or essentially no effect. A suboptimal dose of a combination of baclofen and acamprosate is a dose at which baclofen and acamprosate, when used in a combination consisting of baclofen and acamprosate, have low or essentially no effect under the tested experimental conditions. The effect may be determined in vitro or in vivo, such as in animal model of cognitive impairment. As an example, such test may comprise behavioral tests, spontaneous alternation performance or passive avoidance test, in mice injected intracerebroventricularly with $A\beta$ peptide. These tests are further detailed in the examples. Suboptimal doses more particularly refer to doses lower than those commonly used, such as dosage contemplated for or used in clinical trials, or usually prescribed, preferably ½ of commonly used or therapeutic doses, ⅓ of commonly used or therapeutic doses, ¼, ⅕, or even more preferably 1/10 of commonly used or therapeutic doses. In particular examples, doses as low as 1/20, 1/30, 1/50, 1/100, or even lower, of commonly used therapeutic doses are used. A preferred dosage corresponds to amounts from 1% up to 50% of those usually prescribed for long-term maintenance treatment. The most preferred dosage may correspond to amounts from 1% up to 10% of those usually prescribed for long-term maintenance treatment. The term "suboptimal dose(s)" may be used in reference to one compound, any combination of compounds or any compound within a combination of compounds. At such suboptimal dosages, the compound or combination of compounds would exhibit lower to no side effect, while the combination(s) according to the invention are fully effective in treating AD or AD related disorders. Reducing side effects of the treatment is particularly interesting in chronic neurological disease, such AD or AD related disorders, for which treatment is administered for long periods.

The term "combination or combinatorial treatment/therapy" designates a treatment wherein idalopirdine, baclofen and acamprosate are co-administered to a subject to cause a biological effect. In a combined therapy according to this invention, the compounds may be administered together or separately, at the same time, sequentially or subsequently.

In a particular embodiment, the combination therapy comprises the separate administration of each of idalopirdine, baclofen and acamprosate.

In another particular embodiment, the combination therapy comprises the separate administration of idalopirdine, on the one hand, and baclofen and acamprosate, on the other hand.

In another particular embodiment, the combination therapy comprises the separate administration of baclofen, on the one hand, and idalopirdine and acamprosate, on the other hand.

In a further particular embodiment, the combination therapy comprises the separate administration of acamprosate, on the one hand, and idalopirdine and baclofen, on the other hand.

Also, each of idalopirdine, baclofen and acamprosate may be administered through different routes and protocols.

The combination therapies of the invention also encompass "add-on" therapies, where the subject is already under treatment with some (one or more) of the compounds of a combination of the invention, and the treatment comprises administering the other(s). For instance, in a subject under treatment with idalopirdine, the combination treatment of the invention comprises administering baclofen and acamprosate to the subject.

In an alternative embodiment, the combination therapy comprises the simultaneous administration of idalopirdine, baclofen and acamprosate, as a single formulation.

Within the context of this invention, the designation of a specific drug or compound is meant to include not only the specifically named molecule, but also any pharmaceutically acceptable salt, hydrate, derivative, isomer, racemate, enantiomerically pure composition, conjugate, or prodrug thereof, of any chemical purity.

The term "prodrug" as used herein refers to any functional derivatives (or precursors) of a compound of the present invention, which, when administered to a biological system, generates said compound as a result of e.g., spontaneous chemical reaction(s), enzyme catalysed chemical reaction(s), and/or metabolic chemical reaction(s). Prodrugs typically have the structure X-drug wherein X is an inert carrier moiety and drug is the active compound. Usually, the prodrug is devoid of activity or less active than the drug and the drug is released from the carrier in vivo. Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge [28-32]. Furthermore, the preparation of prodrugs may be performed by conventional methods known by those skilled in the art. Methods which can be used to synthesize other prodrugs are described in numerous reviews on the subject [28-35]. For example, arbaclofen placarbil is listed in ChemID plus Advance database (website: chem.sis.nlm.nih.gov/chemidplus/) and arbaclofen placarbil is a well-known prodrug of baclofen [36,37].

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. For example, homotaurine is a deacetylated derivative of acamprosate. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm.nih.gov/search/) or DrugBank (http://www.drugbank.ca/) [38]. In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector [39,40] available online (http://www.ebi.ac.uk/thornton-srv/software/SMSD/). Preferred derivatives should be both structurally and functionally related to a parent compound, i.e., they should also retain at least part of the activity of the parent drug, more preferably they should have a protective activity against Abeta toxicity and/or impairment of cognitive function.

The term "derivative" also includes metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, preferably that has a protective activity against Abeta toxicity and/or impairment of cognitive function.

The term "salt" refers to a pharmaceutically acceptable and relatively non-toxic, inorganic or organic acid addition salt of a compound of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartaric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalent, some may have, among others, increased solubility or bioavailability properties. Salt selection is now a common standard operation in the process of drug development as taught by Stahl and Wermuth in their handbook [41]. A particularly preferred salt for use in the present invention is acamprosate calcium.

In a preferred embodiment, the designation of a compound is meant to designate the compound per se, as well as any pharmaceutically acceptable salt, hydrate, isomer, racemate, isomer, enantiomerically pure composition, ester or ether thereof.

In a more preferred embodiment, the designation of a compound is meant to designate the compound as specifically designated per se, as well as any pharmaceutically acceptable salt thereof.

In a particular embodiment, a sustained-release formulation of a compound is used.

Illustrative CAS numbers for idalopirdine, baclofen, acamprosate are provided in Table 1 below. Table 1 cites also, in a non-limitative way, common salts, racemates, isomers, enantiomerically pure compositions, prodrugs, metabolites or derivatives of the compounds according to the invention.

TABLE 1

| Drug | CAS Numbers | Class or Tanimoto similarity index |
|---|---|---|
| Acamprosate and related compounds | | |
| Acamprosate | 77337-76-9; 77337-73-6 | NA |
| Homotaurine | 3687-18-1 | 0.73 |
| Ethyl dimethyl ammonio propane sulfonate | 160255-06-1 | 0.77 |
| Taurine | 107-35-7 | 0.5 |
| Baclofen and related compounds | | |
| Baclofen | 1134-47-0; 66514-99-6; 69308-37-8; 70206-22-3; 63701-56-4; 63701-55-3 | NA |
| 3-(p-chlorophenyl)-4-hydroxybutyric acid | 52977-95-4 | Metabolite |
| Arbaclofen placarbil | 847353-30-4 | Prodrug |
| Idalopirdine | | |
| Idalopirdine | 467458-02-2; 467459-31-0 | NA |

NA: not applicable

Specific examples of prodrugs of baclofen are given in Hanafi [42], particularly baclofen esters and baclofen ester carbamates, which are of particular interest for central nervous system targeting. Hence such prodrugs are particularly suitable for compositions of this invention. Arbaclofen placarbil as mentioned before is also a well-known prodrug and may thus be used instead of baclofen in compositions of the invention. Other prodrugs of baclofen can be found in the following patent applications: WO2010102071, US2009197958, WO2009096985, WO2009061934, WO2008086492, US2009216037, WO2005066122, US2011021571, WO2003077902 and WO2010120370, that can be used instead of baclofen in the compositions of the invention.

Useful prodrugs for acamprosate such as pantoic acid ester neopentyl sulfonyl esters, neopentyl sulfonyl esters prodrugs or masked carboxylate neopentyl sulfonyl ester prodrugs of acamprosate are notably listed in WO2009033069, WO2009033061, WO2009033054 WO2009052191, WO2009033079, US2009/0099253, US2009/0069419, US2009/0082464, US2009/0082440 and US2009/0076147, that can be used instead of acamprosate in the compositions of the invention.

Idalopirdine is also known as LUAE58054.

DESCRIPTION OF THE INVENTION

Preferred combinations of the invention comprise idalopirdine, baclofen and acamprosate, wherein idalopirdine is provided at a suboptimal dose, for combined, separate, sequential or subsequent administration.

As discussed above, the drug combinations of the invention have a strong unexpected effect on several biological processes involved in neurological disorders. The inventors have surprisingly discovered that these new compositions can simultaneously, in a synergistic manner, attenuate Abeta toxicity and/or attenuate or reverse impairment of cognitive functions. The examples show that a combination therapy of the invention efficiently protects cells in vivo against Abeta intoxication and/or cognitive impairment, even when each compound is used at suboptimal doses, therefore avoiding possible side effects.

In particular, in an in vivo model of cognitive impairment, the examples show that a combination of idalopirdine, baclofen and acamprosate, efficiently and synergistically reversed the impairment of cognitive functions induced by Aβ(25-35) toxicity.

These drug combinations therefore represent novel approaches for treating AD and AD related disorders.

The present invention therefore proposes a novel therapy of AD or AD related disorders, based on combinations of idalopirdine, baclofen and acamprosate, wherein idalopirdine is provided at suboptimal doses.

In a more particular embodiment, the invention relates to a composition comprising, consisting essentially of or consisting of idalopirdine, acamprosate and baclofen, wherein idalopirdine is provided at a suboptimal dose, for use in the treatment of AD or AD related disorders.

In a further embodiment, the invention relates to the use of idalopirdine, baclofen and acamprosate, wherein idalopirdine is provided at suboptimal doses, for the manufacture of a medicament for the treatment of AD or AD related disorders by simultaneous, separate or sequential administration.

In a particular embodiment, the invention relates to the use of these combinations or compositions for treating AD or an AD related disorder in a subject in need thereof.

The experimental section further shows that the compositions of the invention are also efficient in synergistically protecting in vivo neuronal cells from the above stresses underlying Alzheimer's disease or AD related disorders, and improve clinical symptoms such as cognitive impairment in known mice model of cognitive malfunction.

Synergy can be proven through different ways, for instance, by calculating a combinatory index from dose-effect curves of each of the compounds alone and of their combinations [43-45] and/or using the factorial ANOVA test with treatments as factors, indicating whether an interaction between the factors is significant [46]. Synergy may be assessed by methods known by those skilled in the art.

The presented results notably show that the above combination therapies have an important synergistic effect against Abeta toxicity in nervous cells, also linked to oxidative stress, neuroinflammation and/or neuronal cell deaths, and resulting in improving or attenuating cognitive impairment. These combination therapies represent therefore novel and potent methods for treating AD or AD related disorders.

As mentioned above, the invention is particularly suited for treating AD and AD related disorders, as shown in the experimental section by the results related to Abeta oligomer toxicity also linked to oxidative stress, neuroinflammation and/or neuronal cell deaths, and resulting in reversing, improving or attenuating cognitive impairment.

In a particular embodiment, the invention relates to one of the following compositions per se comprising, consisting essentially of or consisting of:
- idalopirdine, baclofen and acamprosate, wherein idalopirdine is provided at suboptimal doses;
- idalopirdine, baclofen and acamprosate wherein idalopirdine is provided at suboptimal doses, and baclofen and/or acamprosate are provided at suboptimal doses;
- idalopirdine, baclofen and acamprosate wherein idalopirdine is provided at suboptimal doses, and baclofen and acamprosate are provided at suboptimal doses;
- idalopirdine, baclofen and acamprosate wherein idalopirdine is provided at suboptimal doses, and the combination of baclofen and acamprosate is provided at suboptimal doses.

The invention also relates to a composition comprising a synergistic amount of idalopirdine, baclofen and acamprosate, or salts, prodrugs or derivatives thereof.

The invention also relates to a composition comprising (i) between 0.05 mg and 100 mg idalopirdine or a salt, prodrug or derivative thereof; (ii) between 0.005 mg and 50 mg baclofen or a salt, prodrug or derivative thereof; and (iii) between 0.0005 mg and 100 mg acamprosate or a salt, prodrug or derivative thereof. Preferably, the invention relates to a composition comprising (i) between 0.05 mg and 30 mg idalopirdine or a salt, prodrug or derivative thereof; (ii) between 6 mg and 15 mg baclofen or a salt, prodrug or derivative thereof; and (iii) between 0.4 mg and 50 mg acamprosate or a salt, prodrug or derivative thereof. Alternatively, the invention preferably relates to a composition comprising (i) between 0.05 mg and 30 mg idalopirdine or a salt, prodrug or derivative thereof; (ii) between 0.005 mg and 5 mg baclofen or a salt, prodrug or derivative thereof; and (iii) between 0.05 mg and 0.3 mg acamprosate or a salt, prodrug or derivative thereof.

In a more particular embodiment, the invention relates to one of the following compositions comprising, consisting essentially of or consisting of:
- idalopirdine, baclofen and acamprosate wherein idalopirdine is provided at suboptimal doses;
- idalopirdine, baclofen and acamprosate wherein idalopirdine is provided at suboptimal doses, and baclofen and/or acamprosate are provided at suboptimal doses;
- idalopirdine, baclofen and acamprosate wherein idalopirdine is provided at suboptimal doses, and baclofen and acamprosate are provided at suboptimal doses;
- idalopirdine, baclofen and acamprosate wherein idalopirdine is provided at suboptimal doses, and the combination of baclofen and acamprosate is provided at suboptimal doses;

for use in the treatment of AD or of an AD related disorder.

As indicated previously, in a combination therapy of this invention, the compounds or drugs may be formulated together or separately, and administered together, separately, sequentially or subsequently.

A further object of this invention resides in the use of a composition or a combination as defined above for the manufacture of a medicament for treating AD or an AD related disorder.

The invention further provides a method for treating AD or an AD related disorder comprising administering to a subject in need thereof an effective amount of a composition or combination as disclosed above.

A further object of the invention is a method of treating AD or an AD related disorder, the method comprising simultaneously, separately, sequentially or subsequently administering to a subject in need thereof an effective amount of a combination as disclosed above.

A further object of the invention is a method of treating AD or an AD related disorder, the method comprising subsequently administering to a subject in need thereof and already treated with a suboptimal amount of idalopirdine, baclofen and acamprosate. A further object of the invention is a method of treating AD or an AD related disorder, the method comprising subsequently administering to a subject in need thereof and already treated with baclofen and acamprosate, a suboptimal amount of idalopirdine.

In a preferred embodiment, the invention relates to a method of treating AD or an AD related disorder in a subject in need thereof, comprising administering simultaneously, separately, sequentially or subsequently to the subject an effective amount of idalopirdine, baclofen and acamprosate, wherein idalopirdine is provided at suboptimal doses.

The compositions of the invention typically comprise one or several pharmaceutically acceptable carriers or excipients. Also, for use in the present invention, the drugs or compounds are usually mixed with pharmaceutically acceptable excipients or carriers.

In this regard, a further object of this invention is a method of preparing a pharmaceutical composition, the method comprising mixing the above compounds in an appropriate excipient or carrier.

In a particular embodiment, the method comprises mixing idalopirdine, baclofen and acamprosate in an appropriate excipient or carrier.

According to preferred embodiments of the invention, as indicated above, the compounds are used as such or in the form of a pharmaceutically acceptable salt, prodrug, derivative, or sustained/controlled release formulation thereof.

Therapy according to the invention may be provided at home, the doctor's office, a clinic, a hospital's outpatient department, or a hospital, so that the doctor can observe the therapy's effects closely and make any adjustments that are needed.

The duration of the therapy depends on the stage of the disease being treated, age and condition of the patient, and how the patient responds to the treatment. The dosage, frequency and mode of administration of each component of the combination can be controlled independently. For example, one compound may be administered orally while the second compound may be administered intramuscularly. Combination therapy may be given in on-and-off cycles that include rest periods so that the patient's body has a chance to recovery from any as yet unforeseen side-effects. The compounds may also be formulated together such that one administration delivers all drugs.

The administration of each compound of the combination may be by any suitable means that results in a concentration of the compound that, combined with the other component(s), is able to ameliorate the patient condition and/or efficiently treat the disease or disorder.

While it is possible for the compounds of the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a numbered dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable and adapted for use for treatment with the combinations of the present invention.

The compound(s) may be contained, in any appropriate amount, in any suitable carrier substance. The compound(s) may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy [47] and the Encyclopedia of Pharmaceutical Technology [48]).

Pharmaceutical compositions according to the invention may be formulated to release the active compound(s) substantially immediately upon administration or at any predetermined time or time period after administration.

The sustained/controlled release formulations include (i) formulations that create a substantially constant concentration of the compound within the body over an extended period of time; (ii) formulations that after a predetermined lag time create a substantially constant concentration of the compound within the body over an extended period of time; (iii) formulations that sustain compound action during a predetermined time period by maintaining a relatively, constant, effective drug level in the body with concomitant minimization of undesirable side effects associated with fluctuations in the plasma level of the active drug substance; (iv) formulations that localize compound action by, e.g., spatial placement of a controlled release composition adjacent to or in the diseased tissue or organ; and (v) formulations that target compound action by using carriers or chemical derivatives to deliver the drug to a particular target cell type.

Administration of drugs in the form of a sustained/controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain sustained/controlled release in which the rate of release outweighs the rate of metabolism of the compound in question. Controlled release may be obtained by appropriate selection of various formulation parameters and ingredients, including, e.g., various types of controlled release compositions and coatings. Thus, the compound is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active compound substance in a predetermined pattern (e.g., in order to achieve a controlled release formulation) or it may be adapted not to release the active compound substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology [51].

Drugs/compounds may be mixed together in the tablet, or may be partitioned. For example, a first compound is contained on the inside of the tablet, and a second compound is on the outside, such that a substantial portion of the second compound is released prior to the release of the first compound.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders, granulates, micro- or nano-particles may be prepared using the ingredients mentioned above under tablets and capsules in a conventional manner. Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition(s) may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active compound(s), the composition may include suitable parenterally acceptable carriers and/or excipients. The active compound(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active compound(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compound(s) is/are only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active compound(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. In this regard, for rectal application, suitable dosage forms for a composition include suppositories (emulsion or suspension type), and rectal gelatin capsules (solutions or suspensions). In a typical suppository formulation, the active compound(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Slow Release Formulations

Any of the compounds of the combinatorial therapy of the invention may be used in slow release formulations, and/or formulated with agents that modify tissue distribution or bioavailability. More particularly, when applicable, one or more compound(s) of the therapy of the invention are formulated with drug eluting polymer or biomolecules or micelles or liposome-forming lipids or oil in water emulsions, or pegylated or solid nanoparticles or microparticles for oral or parenteral or intrathecal administration to modify tissue distribution or bioavailability. Specific examples of such formulating agents include PGA, PLGA, cyclodextrins, albumin or protein carriers, nano and microparticles, liposomes, emulsions, and PEG.

Conjugates

In combination therapies of this invention, the compounds may be associated in pharmaceutical compositions in different ways. They may be mixed together as separate entities. They may be formulated separately. They may also be linked, covalently or non-covalently, with or without a linker. In a particular embodiment, at least two compounds are linked, preferably through a cleavable or non-cleavable linker.

Dosages and Duration of the Treatment

It will be appreciated that the drugs/compounds of the combination(s) may be administered concomitantly, either in the same or different pharmaceutical formulation, sequentially or subsequently. If there is sequential or subsequent administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the compounds in a combination of this invention include, e.g., amounts that are effective for reducing AD, or AD related disorders, symptoms, halting or slowing the progression of the disease once it has become clinically manifest, or prevention or reduction of the risk of developing the disease.

The active drugs of the present invention may be administered in divided doses, for example two or three times daily. Moreover, different frequency of administration may be used for each compound, e.g., one compound may be administered once daily whereas the other compounds may be administered twice daily. A single administration of a composition of idalopirdine per day, associated with a twice daily administration of a composition of baclofen and acamprosate is preferred. As an alternative embodiment, a single daily dose of each compound in the combination is preferred, with a single daily dose of all drugs in a single pharmaceutical composition (unit dosage form) being most preferred. As a further preferred alternative embodiment, compositions of idalopirdine, baclofen and acamprosate are administered twice a day.

Administration can be repeated for several days to several years, and may even be for the life of the patient. Chronic or at least periodically repeated long-term administration is indicated in most cases.

Likewise, administration can also be once every two days, three to two days per week or once weekly. There also, different frequency of administration may be used for each compound.

The term "unit dosage form" refers to physically discrete units (such as capsules, tablets, loaded syringe cylinders, shaker cups, ampoule) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the disease, the risk of potential side effects considering the general health status of the person to be treated. Additionally, pharmacogenomic (the effect of genotype on the pharmacokinetic, pharmacodynamic or efficacy profile of a therapeutic) information about a particular patient may affect the dosage used.

Except when responding to especially impairing cases, where higher dosages may be required, the preferred dosage of each drug in the combination will usually lie within the range of doses not above the dosage usually prescribed for long-term maintenance treatment or proven to be safe in phase 3 clinical studies.

As previously emphasized, one remarkable advantage of the invention is that idalopirdine, and baclofen and/or acamprosate, and combination of baclofen and acamprosate may be used at suboptimal doses in a combination therapy, while producing, in combination, a substantial clinical benefit to the patient. Accordingly, a particular advantage of the invention lies in the ability to use sub-optimal doses of each compound, i.e., doses which are lower than therapeutic doses usually prescribed or commonly used, preferably ½ of therapeutic doses, more preferably ⅓, ¼, ⅕, ⅙, ⅐, ⅛, ⅑ or even more preferably ⅒ of therapeutic or commonly used doses. In particular examples, doses as low as 1/20, 1/30, 1/50, 1/100, or even lower, of therapeutic doses are used.

At such sub-optimal dosages, the compounds would exhibit lower to no side effect, while the combination(s) according to the invention are fully effective in treating neurological disorders.

A preferred dosage corresponds to amounts from 1% up to 50% of those usually prescribed or used for long-term maintenance treatment.

The most preferred dosage may correspond to amounts from 1% up to 10% of those usually prescribed or used for long-term maintenance treatment.

Specific examples of dosages of compounds for use in the invention are provided below:

acamprosate between 0.0005 mg and 100 mg/day, preferably less than 50 mg/day, preferably less than 40 mg/day, preferably less than 10 mg/day, preferably less than 1 mg/day, preferably less than 0.8 mg/day, preferably less than 0.75 mg/day, more preferably less than 0.6 mg/day, even more preferably less than 0.5 mg/day, preferably less than 0.3 mg/day, preferably less than 0.2 mg/day, preferably less than 0.1 mg/day, more preferably less than 0.05 mg/day, even more preferably less than 0.001 mg/day such dosages being particularly suitable for oral administration;

baclofen between 0.005 mg and 100 mg/day, preferably less than 50 mg/day, preferably less than 30 mg/day, preferably less than 20 mg/day, preferably less than 15 mg/day, more preferably less than 10 mg/day, even more preferably less than 7 mg/day, preferably less than 5 mg/day, preferably less than 4 mg/day, preferably less than 3 mg/day, preferably less than 2 mg/day, preferably less than 1 mg/day, more preferably less than 0.1 mg/day, even more preferably less than 0.01 mg/day, such dosages being particularly suitable for oral administration;

idalopirdine between 0.05 mg and 100 mg/day, preferably less than 70 mg/day, more preferably less than 50 mg/day, even more preferably less than 40 mg/day, preferably less than 30 mg/day, preferably less than 20 mg/day, preferably less than 15 mg/day, preferably less than 10 mg/day, preferably less than 5 mg/day, more preferably less than 1 mg/day, even more preferably less than 0.1 mg/day, such dosages being particularly suitable for oral administration.

Pharmaceutical compositions can be formulated to comprise, typically in unit dosage form:

acamprosate between 0.0005 mg and 100 mg, preferably less than 50 mg, preferably less than 40 mg, preferably less than 10 mg, preferably less than 1 mg, preferably less than 0.8 mg, preferably less than 0.75 mg, more preferably less than 0.6 mg, even more preferably less than 0.5 mg, preferably less than 0.3 mg, preferably less than 0.2 mg, preferably less than 0.1 mg, more preferably less than 0.05 mg, even more preferably less than 0.001 mg such dosages being particularly suitable for oral administration;

baclofen between 0.005 mg and 100 mg, preferably less than 50 mg, preferably less than 30 mg, preferably less than 20 mg, preferably less than 15 mg, more preferably less than 10 mg, even more preferably less than 7 mg, preferably less than 5 mg, preferably less than 4 mg, preferably less than 3 mg, preferably less than 2 mg, preferably less than 1 mg, more preferably less than 0.1 mg, even more preferably less than 0.01 mg, such dosages being particularly suitable for oral administration;

idalopirdine between 0.05 mg and 100 mg, preferably less than 70 mg, more preferably less than 50 mg, even more preferably less than 40 mg, preferably less than 30 mg, preferably less than 20 mg, preferably less than 15 mg, preferably less than 10 mg, preferably less than 5 mg, more preferably less than 1 mg, even more preferably less than 0.1 mg, such dosages being particularly suitable for oral administration.

Moreover, pharmaceutical compositions of the invention can be formulated to comprise, as active ingredient:

acamprosate in an amount from between 0.00001 µg to 2 mg/kg of human subject, preferably less than 1 mg/kg of human subject, preferably less than 0.5 mg/kg of human subject, preferably less than 0.1 mg/kg of human subject, preferably less than 0.05 mg/kg of human subject, preferably less than 0.01 mg/kg of human subject, preferably less than 0.007 mg/kg of human subject, preferably less than 0.006 mg/kg of human subject, more preferably less than 0.005 mg/kg of human subject, even more preferably less than 0.003 mg/kg of human subject, preferably less than 0.0025 mg/kg of human subject, preferably less than 0.002 mg/kg of human subject, preferably less than 0.001 mg/kg of human subject, more preferably less than 0.001 mg/kg of human subject, such dosages being particularly suitable for oral administration;

baclofen in an amount from between 0.0001 mg and 2 mg/kg of human subject, preferably less than 1 mg/kg of human subject, preferably less than 0.8 mg/kg of human subject, preferably less than 0.6 mg/kg of human subject, preferably less than 0.4 mg/kg of human subject, preferably less than 0.2 mg/kg of human subject, preferably less than 0.1 mg/kg of human subject, preferably less than 0.09 mg/kg of human subject, more preferably less than 0.05 mg/kg of human subject, even more preferably less than 0.04 mg/kg of human subject, preferably less than 0.035 mg/kg of human subject, preferably less than 0.02 mg/kg of human subject, preferably less than 0.015 mg/kg of human subject, preferably less than 0.01 mg/kg of human subject, preferably less than 0.001 mg/kg of human subject, such dosages being particularly suitable for oral administration;

idalopirdine in an amount from between 0.001 mg and 1 mg/kg of human subject, preferably less than 0.8 mg/kg of human subject, more preferably less than 0.5 mg/kg of human subject, even more preferably less than 0.4 mg/kg of human subject, preferably less than 0.35 mg/kg of human subject, preferably less than 0.3 mg/kg of human subject, preferably less than 0.2 mg/kg of human subject, preferably less than 0.1 mg/kg of human subject, preferably less than 0.01 mg/kg of human subject, such dosages being particularly suitable for oral administration.

In the context of the present invention, the weight of a human subject is preferably between 40 to 120 kg, more preferably between 50 and 100 kg, and even more preferably between 60 and 80 kg.

Of particular preferences are pharmaceutical compositions as described above wherein the compounds are in synergistic amounts.

In the compositions of the invention, idalopirdine, baclofen and acamprosate may be used in different ratios, more preferably at a weight ratio of approximately 140/15/1.

It will be understood that the amount of the compounds actually administered will be determined by a physician, in the light of the relevant circumstances including the condition or conditions to be treated, the exact composition to be administered, the age, weight, and response of the patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

A—Combination Therapies of the Invention Prevent Cognitive Impairment Induced by $A\beta_{25\text{-}42}$ Toxicity In Vivo The peptide amyloid-β25-35 ($A\beta_{25\text{-}35}$) is the hydrophobic part of the full-length amyloid peptide. Injection of this peptide in the brain ventricles of rodents is known to induce a progressive neurodegenerative process resulting in cognitive impairments. This model is commonly used for diseases involving cognitive impairment symptoms [49-53]. The results of this example showed that a combination of idalopirdine at suboptimal doses, baclofen and acamprosate were not only efficient but had a synergistic effect in protecting treated animals from the neurodegenerative processes due to the injection of toxic peptides.

Treatment Protocol

Male Swiss mice were administered from Day 0 to Day 10 with:

sham product (group 1 and 2);

baclofen, acamprosate and idalopirdine, respectively 0.480 mg/kg, 0.032 mg/kg and 4.5 mg/kg (group 6).

Experiments of FIGS. 1A, 2A and 2C acamprosate 0.032 mg/kg (group 3);

baclofen 0.480 mg/kg (group 4);

idalopirdine 4.5 mg/kg (group 5);

Experiments of FIGS. 1B, 2B and 2D baclofen and acamprosate, respectively 0.480 mg/kg and 0.032 mg/kg (group 3);

acamprosate and idalopirdine, respectively 0.032 mg/kg and 4.5 mg/kg (group 4);

baclofen and idalopirdine, respectively 0.480 mg/kg and 4.5 mg/kg (group 5);

Administration was performed orally by gavage twice a day for each group.

At Day 1, oligomeric $A\beta_{25-35}$ peptide was injected ICV (intracerebroventricular) to provoke amyloid toxicity (group 2, 3, 4, 5 and 6). Sc.$A\beta_{25-35}$ peptide (scrambled $A\beta_{25-35}$ peptide) was injected ICV as negative control of oligomeric $A\beta_{25-35}$ peptide ICV injections (group 1). Male Swiss mice were anesthetized with isoflurane 2.5% and were injected ICV with $A\beta_{25-35}$ peptide (9 nmol/mouse) or Sc.$A\beta$ peptide (9 nmol/mouse), in a final volume of 3 µl/mouse, according to the previously described method [49-53]. Homogeneous oligomeric preparation of the $A\beta_{25-35}$ peptide was performed according to the AMYLGEN's owned procedure (dilution in twice distilled water for 96 h at 37° C.).

At Days 8-10, two different behavioral tests were performed to monitor the effects of the test compounds: the spontaneous alternation procedure in the Y-maze (assessing spatial working memory) at Day 8, and the step-through passive avoidance test at Day 9 (training session) and D 10 (retention session).

Behavioral Analyses—Spontaneous Alternation Performance

Animals were tested for spontaneous alternation performance in the Y-maze, an index of spatial working memory. The Y-maze is made of grey polyvinylchloride. Each arm is 40 cm long, 13 cm high, 3 cm wide at the bottom, 10 cm wide at the top, and converging at an equal angle. Each mouse was placed at the end of one arm and allowed to move freely through the maze during an 8-min session. The series of arm entries, including possible returns into the same arm, was checked visually. An alternation was defined as entries into all three arms on consecutive occasions. The number of maximum alternations was therefore the total number of arm entries minus two and the percentage of alternation was calculated as (actual alternations/maximum alternations)× 100. Parameters included the percentage of alternation (memory index) and total number of arm entries (exploration index) [49-53]

Animals that would show an extreme behavior (Alternation percentage <20% or >90% or number of arm entries <8) were discarded. Usually, it would account for 0-5% of the animals.

Behavioral Analyses—Passive Avoidance Test

All animals were tested for passive avoidance performance, an index of contextual long-term memory. The apparatus was a two-compartment (15×20×15 cm high) box with one illuminated with white polyvinylchloride walls and the other darkened with black polyvinylchloride walls and a grid floor. A guillotine door separated each compartment. A 60 W lamp positioned 40 cm above the apparatus lighted up the white compartment during the experiment. Scrambled footshocks (0.3 mA for 3 s) could be delivered to the grid floor using a shock generator scrambler (MedAssociates, USA). The guillotine door was initially closed during the training session. Each mouse was placed into the white compartment. After 5 s, the door was raised. When the mouse entered the darkened compartment, and placed all its paws on the grid floor, the door was closed and the footshock delivered for 3 s. The step-through latency, that is, the latency spent to enter the darkened compartment, and the number of vocalizations were recorded. The retention test was carried out 24 h after training. Each mouse was placed again into the white compartment. After 5 s, the door was raised. The step-through latency (STL) was recorded up to 300 s. At the end of the experiment animals are placed in the dark compartment (if it is not going by itself), and the time to go back in the white compartment is measured as the Escape Latency (EL) [49-53].

Results—Significant Effect of the Combination Idalopirdine/Baclofen/Acamprosate

All values were expressed as mean±S.E.M. Statistical analyses were performed on the different conditions using one-way ANOVA (F value), followed by the Dunnett's post-hoc multiple comparison test. Passive avoidance latencies did not follow a Gaussian distribution, since upper cut-off times were set. They were therefore analyzed using a non-parametric method the Kruskal-Wallis H test (one-way ANOVA on ranks), followed by a Dunn's multiple comparison test. p<0.05 was considered as statistically significant.

Figure 1:
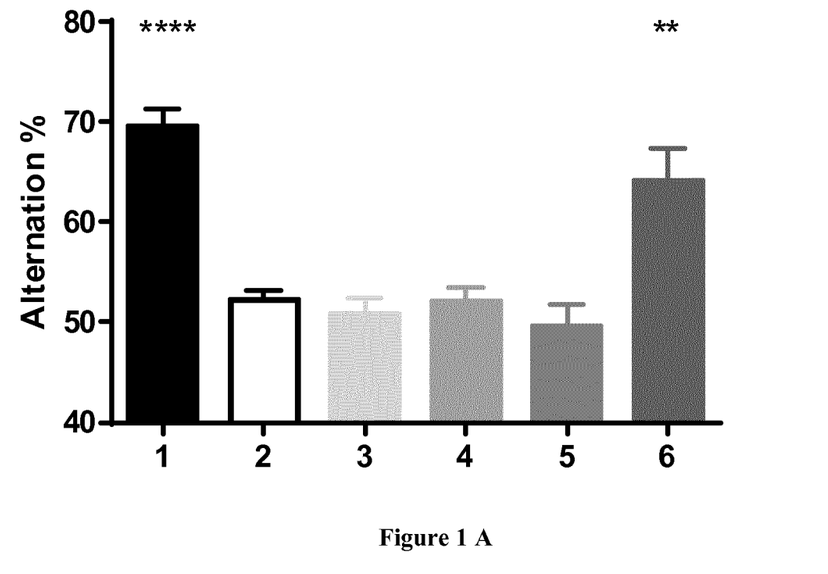
FIGS. 1A-1B: Effect of a combination of idalopirdine, baclofen and acamprosate in vivo in a model of cognitive impairment induced by $A\beta_{25-35}$ toxicity. Cognitive impairment was assessed with respect to spatial working memory (Y-maze test).

As illustrated in FIG. 1, the combination of idalopirdine, baclofen and acamprosate significantly alleviated cognitive deficits induced by $A\beta_{25-35}$ peptides effect in the "spontaneous alternation performance" test in contrast to compounds alone (FIG. 1A) or binary compositions (FIG. 1B).

Figure 2:
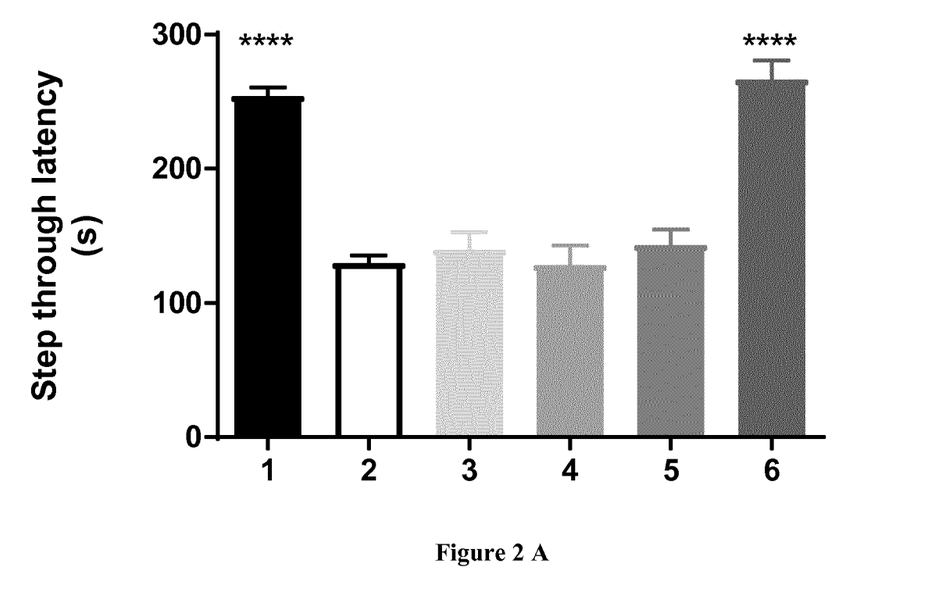
FIGS. 2A-2B-2C-2D: Effect of a combination of idalopirdine, baclofen and acamprosate in vivo in a model of cognitive impairment induced by $A\beta_{25-35}$ toxicity. Cognitive impairment was assessed with respect to contextual long-term memory by assessing passive avoidance performance via the measurement of step-through latency (FIG. 2A-2C) and escape latency (FIG. 2B-2D).

Likewise, in FIG. 2, the combination of idalopirdine, baclofen and acamprosate significantly alleviated cognitive deficits induced by $A\beta_{25-35}$ peptides effect in both "passive avoidance" tests in contrast to compounds alone (FIGS. 2A, 2C) and binary compositions (FIGS. 2B, 2D).

Results—Synergistic Effect of the Combination Idalopirdine/Baclofen/Acamprosate

Two approaches of drug combination analysis were used to assess synergy, the Response Additivity analysis and the Bliss Independence model.

The Response Additivity analysis compares the observed combination effect to an expected additive effect [54].

The Bliss Independence model is an effect-based approach following the principle that drug effects are outcomes of probabilistic processes. It allows comparing the observed combinational effect to the expected additive effect given by the common formula for probabilistic independence requiring mean drug effects between 0 and 1. Data were thus normalized to the control group (1) and vehicle-treated mice (0). And when a mean drug effect was <0, a t-test was done to check whether it was significantly different from 0. If not, the CI of Bliss could then be calculated by replacing the mean drug effect by 0 (Bliss modified) (see table 2). For this approach, Combination Index (CI) were calculated. Briefly, CI compares the dosages of a given combination to those expected to obtain the same combination effect under a simple additive assumption, and offers a quantitative definition for additive effect (CI=1), synergism (CI<1), or antagonism (CI>1) in drug combinations (Loewe).

In order to determine whether the combination of 3 drugs (named trio) exhibited a synergistic effect compared to combinations of 2 drugs (named duos) or to single drugs that compose the trio, four successive CI were calculated. Synergism was certified only if those 4 CI were <1.

Starting with the Response Additivity analysis, the combination of Idalopirdine, Baclofen and Acamprosate, resulted in a synergistic improvement of the mice behavior in all three behavioral tests against any compositions of two compounds, and the third compound as illustrated in table 2.

TABLE 2

| Test | [Drug A] versus [Drug B + Drug C] | | | Combinatorial response effect | |
|---|---|---|---|---|---|
| | Drug A | Drug B | Drug C | RA p-value | RA Estimate |
| Y Maze | IDA_BCL_ACA | IDA_BCL | ACA | 8.37e-05 | 94 |
| | | IDA_ACA | BCL | 0.0169 | 54.5 |
| | | BCL_ACA | IDA | 0.00518 | 72.8 |
| STL | IDA_BCL_ACA | IDA_BCL | ACA | 8.21e-09 | 134 |
| | | IDA_ACA | BCL | 9.01e-08 | 128 |
| | | BCL_ACA | IDA | 1.18e-05 | 94 |
| EL | IDA_BCL_ACA | IDA_BCL | ACA | 3.13e-05 | 106 |
| | | IDA_ACA | BCL | 4.58e-05 | 112 |
| | | BCL_ACA | IDA | 0.0931 | 66.9 |

Wherein ACP means Acamprosate, BCL means Baclofen, IDA means Idalopirdine, STL means Step-Through Latency and EL means Escape Latency.

As regards the Bliss Independence model, the combination of idalopirdine, baclofen and acamprosate also resulted in a synergistic improvement of the mice behavior in all three behavioral tests. In particular, the CI Bliss modified were respectively: (i) 0.163 for the Y-Maze test; (ii) 0.152 for the Step Through Latency test and (iii) 0.303 for the Escape Latency test.

REFERENCES

1 Crook R, Verkkoniemi A, Perez-Tur J, Mehta N, Baker M, Houlden H, Farrer M, Hutton M, Lincoln S, Hardy J, Gwinn K, Somer M, Paetau A, Kalimo H, Ylikoski R, Poyhonen M, Kucera S & Haltia M (1998) A variant of Alzheimer's disease with spastic paraparesis and unusual plaques due to deletion of exon 9 of presenilin 1. *Nat. Med.* 4, 452-5.

2 Houlden H, Baker M, McGowan E, Lewis P, Hutton M, Crook R, Wood N W, Kumar-Singh S, Geddes J, Swash M, Scaravilli F, Holton J L, Lashley T, Tomita T, Hashimoto T, Verkkoniemi A, Kalimo H, Somer M, Paetau A, Martin J J, Van Broeckhoven C, Golde T, Hardy J, Haltia M & Revesz T (2000) Variant Alzheimer's disease with spastic paraparesis and cotton wool plaques is caused by PS-1 mutations that lead to exceptionally high amyloid-beta concentrations. *Ann. Neurol.* 48, 806-8.

3 Kwok J B, Taddei K, Hallupp M, Fisher C, Brooks W S, Broe G A, Hardy J, Fulham M J, Nicholson G A, Stell R, St George Hyslop P H, Fraser P E, Kakulas B, Clarnette R, Relkin N, Gandy S E, Schofield P R & Martins R N (1997) Two novel (M233T and R278T) presenilin-1 mutations in early-onset Alzheimer's disease pedigrees and preliminary evidence for association of presenilin-1 mutations with a novel phenotype. *Neuroreport* 8, 1537-42.

4 Verkkoniemi A, Kalimo H, Paetau A, Somer M, Iwatsubo T, Hardy J & Haltia M (2001) Variant Alzheimer disease with spastic paraparesis: neuropathological phenotype. *J. Neuropathol. Exp. Neurol.* 60, 483-92.

5 Citron M (2004) Strategies for disease modification in Alzheimer's disease. *Nat. Rev. Neurosci.* 5, 677-85.

6 Suh Y-H & Checler F (2002) Amyloid precursor protein, presenilins, and alpha-synuclein: molecular pathogenesis and pharmacological applications in Alzheimer's disease. *Pharmacol. Rev.* 54, 469-525.

7 Blacker D, Albert M S, Bassett S S, Go R C, Harrell L E & Folstein M F (1994) Reliability and validity of NINCDS-ADRDA criteria for Alzheimer's disease. The National Institute of Mental Health Genetics Initiative. *Arch. Neurol.* 51, 1198-204.

8 Rossor M N, Fox N C, Freeborough P A & Harvey R J (1996) Clinical features of sporadic and familial Alzheimer's disease. *Neurodegeneration* 5, 393-7.

9 Glenner G G, Wong C W, Quaranta V & Eanes E D (1984) The amyloid deposits in Alzheimer's disease: their nature and pathogenesis. *Appl. Pathol.* 2, 357-69.

10 Ballatore C, Lee V M-Y & Trojanowski J Q (2007) Tau-mediated neurodegeneration in Alzheimer's disease and related disorders. *Nat. Rev. Neurosci.* 8, 663-72.

11 DiLuca M, Bell K F S & Claudio Cuello A (2006) Altered synaptic function in Alzheimer's disease. *Eur. J. Pharmacol.* 545, 11-21.

12 Hardy J A & Higgins G A (1992) Alzheimer's disease: the amyloid cascade hypothesis. *Science* 256, 184-5.

13 Braak H & Braak E (1991) Neuropathological stageing of Alzheimer-related changes. *Acta Neuropathol.* 82, 239-59.

14 Golde T E (2005) The Abeta hypothesis: leading us to rationally-designed therapeutic strategies for the treatment or prevention of Alzheimer disease. *Brain Pathol.* 15, 84-7.

15 Hardy J & Selkoe D J (2002) The amyloid hypothesis of Alzheimer's disease: progress and problems on the road to therapeutics. *Science* 297, 353-6.

16 Selkoe D J (2000) The genetics and molecular pathology of Alzheimer's disease: roles of amyloid and the presenilins. *Neurol. Clin.* 18, 903-22.

17 Zlokovic B V (2008) The blood-brain barrier in health and chronic neurodegenerative disorders. *Neuron* 57, 178-201.

18 Budd Haeberlein S L & Lipton S A (2009) Excitotoxicity in neurodegenerative disease. In *Encyclopedia of neuroscience* (Squire L R, ed), pp. 77-86. Elsevier.

19 Maccioni R B, Farias G, Morales I, Navarrete L (2010 April) The revitalized tau hypothesis on Alzheimer's disease. *Arch Med Res.* 41(3): 226-31

20 McGleenon B M, Dynan K B & Passmore A P (1999) Acetylcholinesterase inhibitors in Alzheimer's disease. *Br. J. Clin. Pharmacol.* 48, 471-480.

21 Parsons C G, Danysz W & Quack G (1999) Memantine is a clinically well tolerated N-methyl-D-aspartate (NMDA) receptor antagonist—a review of preclinical data. *Neuropharmacology* 38, 735-67.

22 Gauthier S & Scheltens P (2009) Can we do better in developing new drugs for Alzheimer's disease? *Alzheimer's Dement.* 5, 489-491.

23 Aliabadi A, Foroumadi A, Mohammadi-Farani A & Garmsiri Mahvar M (2013) Synthesis and Evaluation of Anti-acetylcholinesterase Activity of 2-(2-(4-(2-Oxo-2-phenylethyl)piperazin-1-yl) ethyl)Isoindoline-1,3-dione Derivatives with Potential Anti-Alzheimer Effects. *Iran. J. Basic Med. Sci.* 16, 1049-54.

24 Kaduszkiewicz H & Hoffmann F (2008) Review: cholinesterase inhibitors and memantine consistently but marginally improve symptoms of dementia. *Evid. Based. Ment. Health* 11, 113.

25 Galvin J E (2012) OPTIMIZING DIAGNOSIS AND MANANGEMENT IN MILD-TO-MODERATE ALZHEIMER'S DISEASE. *Neurodegener. Dis. Manag.* 2, 291-304.

26 Lipton S A (2004) Failures and successes of NMDA receptor antagonists: molecular basis for the use of open-channel blockers like memantine in the treatment of acute and chronic neurologic insults. *NeuroRx* 1, 101-10.

27 Lipton S A (2006) Paradigm shift in neuroprotection by NMDA receptor blockade: memantine and beyond. *Nat. Rev. Drug Discov.* 5, 160-70.

28 Stella V J (2007) Prodrugs: challenges and rewards. (A. Press and Springer, eds.) Springer Singapore Pte. Limited, New-York.

29 Wermuth C G (2011) *The Practice of Medicinal Chemistry* Elsevier Science.

30 Pezron I, Mitra A K, Duvvuri S & Tirucherai G S (2002) Prodrug strategies in nasal drug delivery. *Expert Opin. Ther. Pat.* 12, 331-340.

31 Stella V J (2004) Prodrugs as therapeutics. *Expert Opin. Ther. Pat.* 14, 277-280.

32 Stella V J & Nti-Addae K W (2007) Prodrug strategies to overcome poor water solubility. *Adv. Drug Deliv. Rev.* 59, 677-94.

33 Beaumont K, Webster R, Gardner I & Dack K (2003) Design of ester prodrugs to enhance oral absorption of poorly permeable compounds: challenges to the discovery scientist. *Curr. Drug Metab.* 4, 461-85.

34 Higuchi T & Stella V J (1975) *Pro-drugs as Novel Drug Delivery System*, ACS Sympos American Chemical Society, Washington, D.C.

35 Roche E B (1977) *Design of biopharmaceutical properties through prodrugs and analogs: a symposium*, American P The Academy, Washington, D.C.

36 Lal R, Sukbuntherng J, Tai E H L, Upadhyay S, Yao F, Warren M S, Luo W, Bu L, Nguyen S, Zamora J, Peng G, Dias T, Bao Y, Ludwikow M, Phan T, Scheuerman R A, Yan H, Gao M, Wu Q Q, Annamalai T, Raillard S P, Koller K, Gallop M A & Cundy K C (2009) Arbaclofen placarbil, a novel R-baclofen prodrug: improved absorption, distribution, metabolism, and elimination properties compared with R-baclofen. *J. Pharmacol. Exp. Ther.* 330, 911-21.

37 Xu F, Peng G, Phan T, Dilip U, Chen J L, Chernov-Rogan T, Zhang X, Grindstaff K, Annamalai T, Koller K, Gallop M A & Wustrow D J (2011) Discovery of a novel potent GABA(B) receptor agonist. *Bioorg. Med. Chem. Lett.* 21, 6582-5.

38 Wishart D S, Knox C, Guo A C, Cheng D, Shrivastava S, Tzur D, Gautam B & Hassanali M (2008) DrugBank: a knowledgebase for drugs, drug actions and drug targets. *Nucleic Acids Res.* 36, D901-6.

39 Leach A R & Gillet V J *An Introduction to Chemoinformatics* (Springer-Verlag New York Inc, ed.).

40 Rahman S A, Bashton M, Holliday G L, Schrader R & Thornton J M (2009) Small Molecule Subgraph Detector (SMSD) toolkit. *J. Cheminform.* 1, 12.

41 Stahl H & Wermuth C G (2011) *Pharmaceutical salts: Properties, selection, and use,* 2nd ed. (Wiley-VCH, ed.).

42 Hanafi R, Mosad S, Abouzid K, Niess R & Spahn-Langguth H (2011) Baclofen ester and carbamate prodrug candidates: a simultaneous chromatographic assay, resolution optimized with DryLab. *J. Pharm. Biomed. Anal.* 56, 569-76.

43 Chou T-C (2006) Theoretical basis, experimental design, and computerized simulation of synergism and antagonism in drug combination studies. *Pharmacol. Rev.* 58, 621-81.

44 Grabovsky Y & Tallarida R J (2004) Isobolographic analysis for combinations of a full and partial agonist: curved isoboles. *J. Pharmacol. Exp. Ther.* 310, 981-6.

45 Berenbaum M C (1977) Synergy, additivism and antagonism in immunosuppression. A critical review. *Clin. Exp. Immunol.* 28, 1-18.

46 Slinker B K (1998) The statistics of synergism. *J. Mol. Cell. Cardiol.* 30, 723-31.

47 Gennaro A R (2000) *Remington: The Science and Practice of Pharmacy,* 20th ed. (A. D. Gennaro, W. Lippincott, and Wilkins, eds.) Lippincott Williams & Wilkins 48 Swarbrick J & Boylan J C (eds.) *Encyclopedia of Pharmaceutical Technology* Dekker, Marcel, New-York.

49 Maurice T, Lockhart B P, Privat A. Amnesia induced in mice by centrally administered β-amyloid peptides involves cholinergic dysfunction. Brain Res 706, 181-193, 1996

50 Maurice T, Su T P, Privat A. Sigma$_1$ ($\sigma_1$) receptor agonists and neurosteroids attenuate $\beta_{25-35}$-amyloid peptide-induced amnesia in mice through a common mechanism. Neuroscience, 83, 413-428, 1998

51 Meunier J, Ieni J, Maurice T. The anti-amnesic and neuroprotective effects of donepezil against amyloid $\beta_{25-35}$ peptide-induced toxicity in mice involve an interaction with the σ1 receptor. Br J Pharmacol, 149, 998-1012, 2006

52 Villard V, Espallergues J, Keller E, Alkam T, Nitta A, Yamada K, Nabeshima T, Vamvakides A, Maurice T. Anti-amnesic and neuroprotective effects of the aminotetrahydrofuran derivative ANAVEX1-41 against amyloid $\beta_{25-35}$-induced toxicity in mice. Neuropsychopharmacology, 34, 1552-66, 2009

53 Villard V, Espallergues J, Keller E, Vamvakides A, Maurice T. Anti-amnesic and neuroprotective potentials of the mixed muscarinic receptor/sigma$_1$ ($\sigma_1$) ligand ANAVEX2-73, a novel aminotetrahydrofuran derivative. J Psychopharmacol, 25, 1101-17, 2011

54 Foucquier, J. & Guedj, M. Analysis of drug combinations: current methodological landscape. Pharmacol. Res. Perspect. 3, e00149 2015.

55 Wilkinson D, Windfeld K, Colding-Jorgense E, The Lancet Neurology, Volume 13, Issue 11, 1092-1099, Safety and efficacy of idalopirdine, a 5-HT6 receptor antagonist, in patients with moderate Alzheimer's disease (LADDER): a randomised, double-blind, placebo-controlled phase 2 trial

The invention claimed is:

1. A method of treating Alzheimer's disease (AD) or an AD-related disorder comprising administering a combination of compounds comprising idalopirdine, baclofen and acamprosate, or salts, derivatives or prodrugs thereof, to a patient having AD or an AD-related disorder, wherein idalopirdine is provided at a suboptimal dose.

2. The method according to claim 1, wherein baclofen and/or acamprosate, or the salts, derivatives or prodrugs thereof, are provided at suboptimal doses.

3. The method according to claim 2, wherein baclofen and acamprosate, or the salts, derivatives or prodrugs thereof, are provided at suboptimal doses.

4. The method according to claim 1, wherein idalopirdine, or the salt, prodrug or derivative thereof, is provided at a dose between 0.05 mg and 30 mg; and/or baclofen, or the salt, prodrug or derivative thereof, is provided at a dose between 0.005 mg and 5 mg; and/or acamprosate, or the salt, prodrug or derivative thereof, is provided at a dose between 0.0005 mg and 0.3 mg.

5. The method according to claim 1, wherein the compounds are formulated for a separate, simultaneous or sequential administration.

6. The method according to claim 1, wherein the compounds are formulated together.

7. A pharmaceutical composition comprising idalopirdine, baclofen and acamprosate, or salts, derivatives or prodrugs thereof, wherein idalopirdine is provided at a suboptimal dose.

8. The composition according to claim 7, wherein baclofen and/or acamprosate, or the salts, derivatives or prodrugs thereof, are provided at suboptimal doses.

9. The composition according to claim 7, wherein baclofen and acamprosate, or the salts, derivatives or prodrugs thereof, are provided at suboptimal doses.

10. A pharmaceutical composition comprising (i) between 0.05 mg and 30 mg idalopirdine or a salt, prodrug or derivative thereof; (ii) between 0.005 mg and 5 mg baclofen or a salt, prodrug or derivative thereof; and (iii) between 0.0005 mg and 0.3 mg acamprosate or a salt, prodrug or derivative thereof.

11. A method of treating Alzheimer's disease (AD) or an AD-related disorder comprising administering the pharmaceutical composition according to claim 7 to a patient having AD or an AD-related disorder.

* * * * *

UNITED STATES PATENT AND TRADEMARK OFFICE
CERTIFICATE OF CORRECTION

PATENT NO. : 10,736,876 B2
APPLICATION NO. : 16/607418
DATED : August 11, 2020
INVENTOR(S) : Daniel Cohen et al.

It is certified that error appears in the above-identified patent and that said Letters Patent is hereby corrected as shown below:

In the Specification

<u>Column 1,</u>
Line 18, "baclo fen" should read --baclofen--.

<u>Column 26,</u>
Line 39, "61 receptor." should read --σ1 receptor.--.
Line 57, "5-HT6" should read --5-HT$_6$--.

Signed and Sealed this
Ninth Day of February, 2021

Drew Hirshfeld
*Performing the Functions and Duties of the
Under Secretary of Commerce for Intellectual Property and
Director of the United States Patent and Trademark Office*